(12) United States Patent
Pagnin et al.

(10) Patent No.: US 12,117,433 B2
(45) Date of Patent: Oct. 15, 2024

(54) MOBILE UNIT AND METHOD FOR CONTINUOUSLY MONITORING FLOWING COOLING WATER

(71) Applicant: PETRÓLEO BRASILEIRO S.A.—PETROBRAS, Rio de Janeiro (BR)

(72) Inventors: Sergio Pagnin, Rio de Janeiro (BR); Andrea Azevedo Veiga, Rio de Janeiro (BR)

(73) Assignee: Petróleo Brasileiro S. A. - Petrobras, Rio de Janeiro (BR)

( * ) Notice: Subject to any disclaimer, the term of this patent is extended or adjusted under 35 U.S.C. 154(b) by 578 days.

(21) Appl. No.: 17/292,833

(22) PCT Filed: Nov. 11, 2019

(86) PCT No.: PCT/BR2019/050486
§ 371 (c)(1),
(2) Date: May 11, 2021

(87) PCT Pub. No.: WO2020/097705
PCT Pub. Date: May 22, 2020

(65) Prior Publication Data
US 2021/0405013 A1   Dec. 30, 2021

(30) Foreign Application Priority Data
Nov. 12, 2018   (BR) .......................... 102018073233-1

(51) Int. Cl.
*G01N 33/18*   (2006.01)
*C02F 1/00*   (2023.01)
(Continued)

(52) U.S. Cl.
CPC ............. *G01N 33/18* (2013.01); *C02F 1/008* (2013.01); *G01N 1/14* (2013.01); *G05D 21/02* (2013.01);
(Continued)

(58) Field of Classification Search
None
See application file for complete search history.

(56) References Cited

U.S. PATENT DOCUMENTS

| | | | |
|---|---|---|---|
| 4,383,920 A * | 5/1983 | Muller | C02F 9/00 210/93 |
| 8,211,296 B2 * | 7/2012 | Angelilli | C02F 1/008 210/194 |

(Continued)

FOREIGN PATENT DOCUMENTS

| | | |
|---|---|---|
| EP | 0497518 A1 | 8/1992 |
| WO | 9503997 A1 | 2/1995 |

(Continued)

OTHER PUBLICATIONS (Mar. 20, 2018) "Agua na Petrobras", accessed at<https://www.google.com/search?client=firefox-b-d&q=inurl%3Ahttp%3A%2F%2Fwww.petrobras.com.br+%E2%80%BA+lumis+%E2%80%BA+portal+%E2%80%BA+file+%E2%80%BA+fileDownload%C3%81GUA+NA+PETROBRAS&as_qdr=y15>, accessed on Jan. 22, 2020, 26-27.

(Continued)

*Primary Examiner* — John E Breene
*Assistant Examiner* — Nigel H Plumb
(74) *Attorney, Agent, or Firm* — Mintz, Levin, Cohn, Ferris, Glovsky and Popeo, P.C.

(57) ABSTRACT

A continuous mobile monitoring unit of a flow of cooling water includes a means to extract a flow of cooling water, means to analyze a plurality of parameters of the cooling (Continued)

water by means of diverse analytical techniques, generating results relating to each one of the parameters analyzed, and means to return the flow of cooling water to the cooling system. In addition, a method of continuous monitoring of the flow of cooling water includes the stages of: extracting a flow of cooling water, analyzing a plurality of parameters of the cooling water by means of diverse analytical techniques, generating results relating to each one of the parameters analyzed, and returning the cooling water to the cooling system.

19 Claims, 3 Drawing Sheets

(51) Int. Cl.
*G01N 1/14* (2006.01)
*G05D 21/02* (2006.01)
*C02F 103/02* (2006.01)

(52) U.S. Cl.
CPC .. *C02F 2103/023* (2013.01); *C02F 2209/008* (2013.01); *C02F 2209/04* (2013.01); *C02F 2209/05* (2013.01); *C02F 2209/06* (2013.01); *C02F 2209/11* (2013.01); *C02F 2209/22* (2013.01); *C02F 2209/29* (2013.01); *C02F 2209/36* (2013.01)

(56) References Cited

U.S. PATENT DOCUMENTS

| | | | |
|---|---|---|---|
| 8,388,850 B2* | 3/2013 | Delano | C02F 9/00 250/435 |
| 2012/0021401 A1* | 1/2012 | Ulitzur | G01N 35/04 435/286.5 |

FOREIGN PATENT DOCUMENTS

| | | |
|---|---|---|
| WO | 2009123749 A2 | 10/2009 |
| WO | 2020097705 A1 | 5/2020 |

OTHER PUBLICATIONS (Mar. 20, 2018) "Google Search Page", acessed at <https://www.google.com/search?client=firefox-b-d&q=inurl%3Ahttp%3A%2F%2Fwww.petrobras.com.br+%E2%80%BA+lumis+%E2%80%BA+portal+%E2%80%BA+file+%E2%80%BA+fileDownload%C3%81GUA+NA+PETROBRAS&as_qdr=y15>, accessed on Jan. 22, 2020.

(2012) "Programacao e Projeto Fisico de Unidade Movel Para o Apoio ao Controle da Qualidade da Agua Para Consumo Humano—UMCQA", Fundacao Nacional de Saude, access from <https://bvsms.saude.gov.br/bvs/publicacoes/programacao_projeto_fisico_movel_controle_qualidade_agua_humano.pdf>, 53 pages.

Trovati, Joubert (Sep. 2004) "Tratamento De Agua De Resfriamento", Tratamento de agua de sistemas de resfriamento—online course, 80-89.

* cited by examiner

MOBILE UNIT AND METHOD FOR CONTINUOUSLY MONITORING FLOWING COOLING WATER

CROSS-REFERENCE TO RELATED APPLICATIONS

This application is a U.S. national phase filing under 35 U.S.C. § 371 of International Application No. PCT/BR2019/050486, filed Nov. 11, 2019 and claims priority to Brazilian Application No. BR 102018073233-1, filed Nov. 12, 2018. The entire contents of the prior applications are incorporated herein by reference in their entity.

FIELD OF THE INVENTION

The present invention relates to technologies in the treatment and reuse of water. More particularly, the present invention relates to a monitoring unit of cooling water of cooling systems and a method associated therewith.

BACKGROUND TO THE INVENTION

The monitoring of cooling systems, in particular of the cooling water, employed in cooling systems is, in general, carried out by means of laboratory analyses upon samples collected routinely and by means of the assessment of the corrosivity thereof obtained through rates of corrosion of test bodies in contact with a specific medium.

However, the chemical analyses carried out on samples collected in the field depict an event in the past. The same occurs in relation to corrosivity, the assessment whereof is obtained following the exposure of the test body in contact with the water for a period, normally, of approximately 30 days.

Consequently, those operational perturbations which may arise during the sampling intervals cannot be observed by these techniques.

Alternative monitoring techniques in real time are commercially available, however they are little utilized by virtue of the associated cost, or, when applied, are partially integrated into other parameters of monitoring in real time such as, for example, conductivity and oxidation-reduction potential.

Monitoring of the quality of the cooling water is generally achieved following chemical analyses upon samples collected in the field, this including transport, receipt, execution and issue of the result. These actions require the availability of professional persons and resources.

The analytical tests, indispensable to ensure the quality and the suitability of the cooling water to the operational requirements, form part of the routine of monitoring the quality of the water of cooling systems.

Correlation between the corrosive process, the physicochemical parameters and the operational changes is wanting in the current scenario. At the present time there is great delay in the period of interpretation of the data, as a function of the limitations inherent to the execution of each of the techniques.

The synergy between both techniques is fundamental for the proper mitigation of the corrosive, incrustation or microbiological processes. The monitoring of the change, in real time, of parameters responsible for phenomena of deterioration of equipments would permit corrective responses in the chemical treatment of cooling systems. This renders possible the indirect increase in the working life of equipments through immediate adjustments to the dosage of the chemical products.

At the present time the chemical treatment of cooling systems is entirely dependent upon commercial products made available by service provision companies. The companies acting in this area, outsourced cooling water treatment services, are principally focused upon the monitoring of the chemical treatment, having a limited technical coverage in relation to the impacts of contaminants upon the integrity of the equipments, this generating inadequate diagnoses of the corrosive, incrustation or microbiological processes and may also impact upon the reduction of operational reliability and reduce operational safety.

The state of the art comprises documents revealing devices and systems rendering possible specific analyses upon water samples, as shall be presented below.

The document WO2010086857A1 reveals a disposable cartridge for use in analysis of samples in an automated water quality monitoring analyzer possessing containers for reagents and a reaction chamber installed upon a platform. The reaction chamber is designed such as to be displaced upon the platform and, consequently, receive the appropriate reagents for the execution of the analysis of the water.

The document EP497518A1 reveals improvements in the analytical procedure for monitoring cooling water circulating in a nuclear reactor cooling system. The improvement consists in the pretreatment of the water samples, through the adjustment of the pH thereof, such as to stabilize it, maintaining in solution the ions which it is desired be studied. The adjustment of pH is executed, preferentially, through the injection of carbon dioxide ($CO_2$).

The document WO1995003997A1 reveals an automatic system for the injection of chemical products and for blown-down of the cooling water. The system is constituted by two sensors. The first measures the oxidation-reduction potential of the water and acts directly in the injection of chemical products when the oxidation-reduction potential measured attains a predetermined value. The second sensor measures the conductivity of the water and actions the opening of the blown-down valve of the system when the conductivity measured attains a predetermined value.

However, the devices described in such documents do not describe a mobile equipment capable of monitoring up to eleven parameters related to the physicochemical assessment of cooling systems, adjusting chemical products dosage, testing new water treatment formulations, or optimizing the dosages of the products employed.

In addition, the state of the art demonstrates a demand for a cooling water monitoring system providing the potential reduction in the quantity of analyses executed in external laboratories, optimizing the monitoring, and an indication in real time of possible deviations of the characteristics of the water, rendering possible actions prior to damage and/or corrective actions in the system as a whole.

As shall be better detailed below, the present invention has the objective of solving the aforedescribed problems of the state of the art in a practical and efficient manner.

SUMMARY OF THE INVENTION

The object of the present invention is to provide a monitoring system for liquids, presenting a reduction in the demand for analyses in external laboratories and indicating in real time possible deviations in the characteristics of the liquid, rendering possible corrective actions to prevent damage to the system.

In order to achieve the aforedescribed object, the present invention provides a mobile unit for flowing cooling water continuous monitoring comprising: means to extract a flow of cooling water, means to analyze a plurality of parameters of the cooling water by means of a plurality of analytical techniques, generating a plurality of results in relation to each one of the parameters analyzed, and means to return the flow of cooling water to the cooling system.

In addition, the invention furthermore provides a method of continuous monitoring of a flow of cooling water, comprising the stages of: extracting a flow of cooling water, analyzing a plurality of parameters of the cooling water by means of diverse analytical techniques generating results in relation to each one of the parameters analyzed, and returning the flow of cooling water to the cooling system.

BRIEF DESCRIPTION OF THE DRAWINGS

The detailed description presented below makes reference to the appended drawings and the respective reference numbers thereof.

DETAILED DESCRIPTION OF THE INVENTION

In a preliminary manner, it is emphasized that the following description is based upon a preferential embodiment of the invention. As shall be obvious to any person skilled in the art, however, the invention is not limited to this particular embodiment.

In a broader manner, in one specific configuration the mobile cooling water continuous monitoring unit consists of a container wherein there are installed industrial analyzers, programmable logic controller (PLC), supervisory computer, electric panel, dosing pumps, pipework and accessories, in addition to two centrifugal pumps.

Figure 1:
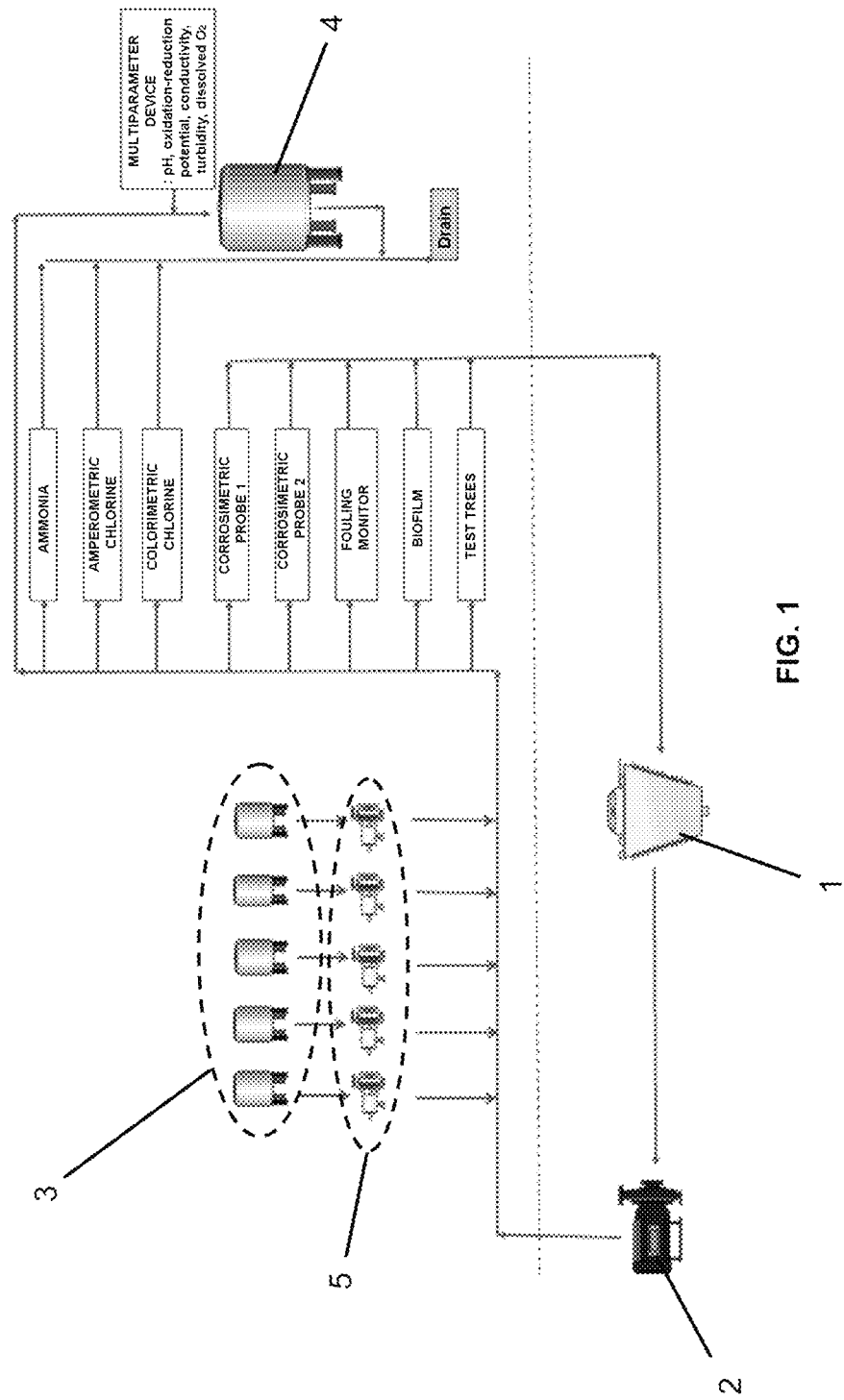
FIG. 1 illustrates a schematic flow diagram of a mobile flowing cooling water monitoring unit according to an optional configuration of the present invention.

FIG. 1 illustrates a schematic flow diagram of a mobile flowing cooling water monitoring unit according to an optional configuration of the present invention.

The mobile cooling water monitoring unit of the invention brings together, in an integrated manner, the instruments required for the acquisition of analytical data relating to the monitoring of the quality of the cooling water.

In a general manner, the mobile monitoring unit of a flow of flowing cooling water operates in line with the cooling system 1 wherein it is applied, extracting and returning cooling water, and incorporates different analytical techniques, having the purpose of facilitating the acquisition of data.

In other words, the continuous flowing cooling water mobile monitoring unit comprises means to extract cooling water, means to analyze a plurality of parameters of the cooling water by means of diverse analytical techniques, generating results relating to each one of the parameters analyzed, and means to return the cooling water to the cooling system 1.

Furthermore, the invention also provides a continuous cooling water monitoring method comprising the stages of extracting a flow of cooling water, analyzing a plurality of parameters of the cooling water by means of diverse analytical techniques, generating results relating to each one of the parameters analyzed, and returning the cooling water to the cooling system 1.

According to one particular configuration, the parameters analyzed may be selected from among: mass loss from test bodies, corrosion rates by means of corrosimetric probes, free residual chlorine, total residual chlorine, dissolved oxygen, pH, oxidation-reduction potential, conductivity, turbidity, biofilm formation and index of deposition.

The method of continuous monitoring of a flow of flowing cooling water furthermore provides, optionally, stages of verifying whether the result of the analysis of each parameter of the cooling water is in conformity with the specification and executing a corrective action for each cooling water parameter falling outside the established standard value.

Having this objective, the monitoring unit may comprise a control system adapted to execute all the actions described in the foregoing paragraph. The control system adopted may be any one known in the state of the art and must be interconnected with, and control, a plurality of valves, pumps 2 and sensors necessary for the system to properly function.

In this respect, it is emphasized that the means for analyzing a plurality of parameters of the cooling water may comprise specific sensors to analyze each parameter of the cooling water. The types and quantities of sensors adopted may vary according to each application, wherein more than one sensor, of more than one analytical technique, may be utilized to analyze the same parameter, if so desired.

In addition, the method of continuous monitoring of a flow of flowing cooling water may comprise a stage of discarding a portion of cooling water collected subsequent to the execution of at least one analysis of a parameter. This stage may be necessary in those cases wherein the process of analysis of the cooling water alters the characteristics of the water, being capable of causing damage to the cooling system 1.

Consequently, the method of the invention renders possible that the cooling water may be continuously monitored such that, when any deviation in the established parameters is identified, a corrective action may be executed.

Various corrective actions may be adopted and, in general, they comprise the injection of a physicochemical agent into the flow of cooling water, preferably downstream from the point of return of the cooling water to the cooling system 1.

The parameters analyzed of the cooling water, together with the analytical techniques adopted, may vary widely such that the options described in the present memorandum are merely suggestions, being modifiable in accordance with each application of the invention.

Optionally, the flowing cooling water mobile monitoring unit may be constructed within a structure of an occupiable container and possess the possibility of displacement. The unit furthermore permits the obtainment of data in diverse industrial plants.

In the specific case illustrated in FIG. 1, the means for analyzing a plurality of cooling water parameters of the mobile continuous monitoring unit of flowing cooling water comprise five tanks of chemical products permitting carrying out performance tests of commercial chemical products or testing innovative formulations in the area of chemical treatment of cooling system water or optimizing dosages of products employed. The number of tanks adopted, clearly, may vary according to each application and the number of analyses to be executed.

In addition to the analytical instruments, the control system of the monitoring unit may comprise a system of operation and supervision constituted by a supply panel (electric panel), emergency (uninterruptible) electric supply, programmable logic controller (PLC), supervisory system, computer and modem. This system will be responsible for the acquisition, processing, storage and transmission of the values generated by the analyzers.

In conformity with that aforedescribed, the monitoring unit is constructed in such manner as to permit the relocation of the same, optionally through the lifting of the unit, fully assembled, and relocation by lorry to the point of interest. Once positioned, the monitoring unit is hydraulically connected to the system, wherein the cooling water is collected downstream of the cooling system 1 (cooling tower) and returns to the system at a point upstream of the cooling system or in the cooling tower.

The mobile monitoring unit may comprise diverse equipments such that said unit may function in the desired manner. These equipments are common to diverse systems and may comprise: centrifugal pumps 2 and hoses, tanks of chemical products 3, dosing pumps of chemical products 5, dwell tank for multiparameter probe 4, electric panel, auxiliary (uninterruptible) energy system, control panel, supervisory computer, air conditioning and bench with sink.

Optionally, the centrifugal pumps 2 may be specified to permit the displacement of the fluid from the point of extraction to the container at an operational flow rate of 10 $m^3/h$, and approximately 50 m flexible hoses of compose the assembly.

The tanks of chemical products 3 are, optionally, five in number, and include mixers, dosing pumps 5, and solenoids. These devices permit the action of chemical products to be tested, individually or conjointly, in the water extracted by the monitoring unit. This permits that tests may be carried out upon commercial chemical products or upon chemical products in the development phase.

In addition to the tanks of chemical products 3, the mobile monitoring unit may comprise a dwell tank 4 associated to a multiparameter probe adapted to measure pH, turbidity, conductivity and oxidation-reduction potential.

The source of supply of the monitoring unit may arise from a location external to the container by means of a weatherproof female three-phase connector connecting the electric panel to the source of energy. This source of energy may be both another electric panel of equal nominal voltage located in the plant, wherein the unit is operating, or a diesel or petrol powered generator supplying the unit in locations whereat no other available source exists.

The electric panel has been configured to operate with three different busbars: two at 220 V, whereof one is for the components fed by the auxiliary energy system (instruments, analyzers and pumps) and the other for the components not supplied by the uninterruptible device (air-conditioning, illumination and sockets), in addition to a further one at 380 V for the stirrers of the tanks of chemical products.

These supply characteristics have been utilized in the model illustrated, however a person skilled in the art will be capable of determining the best configuration for each case. As a consequence, this characteristic does not represent a limitation on the scope of protection of the present invention.

Figure 2:
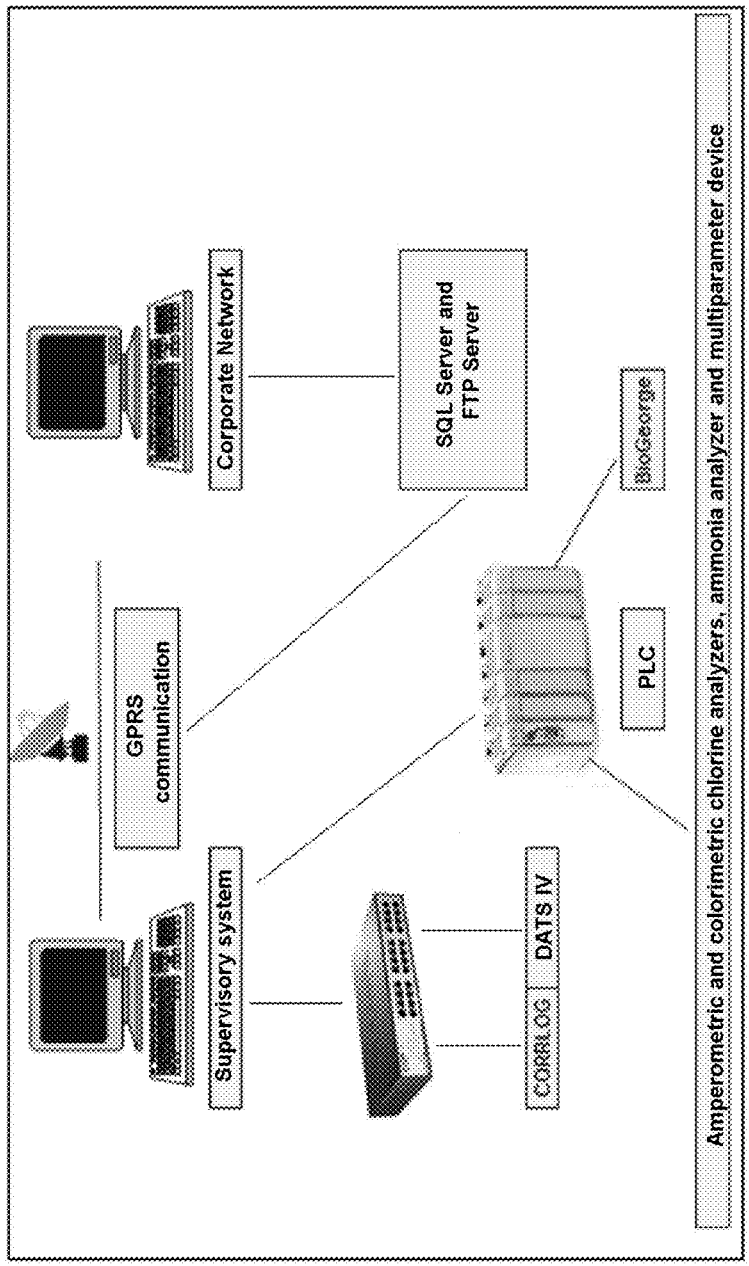
FIG. 2 illustrates a schematic flow diagram of a system of transmission of signals and data according to a specific configuration of the invention.

FIG. 2 shows a schematic flow diagram of a system of transmission of signals and data according to a specific configuration of the invention.

Figure 3:
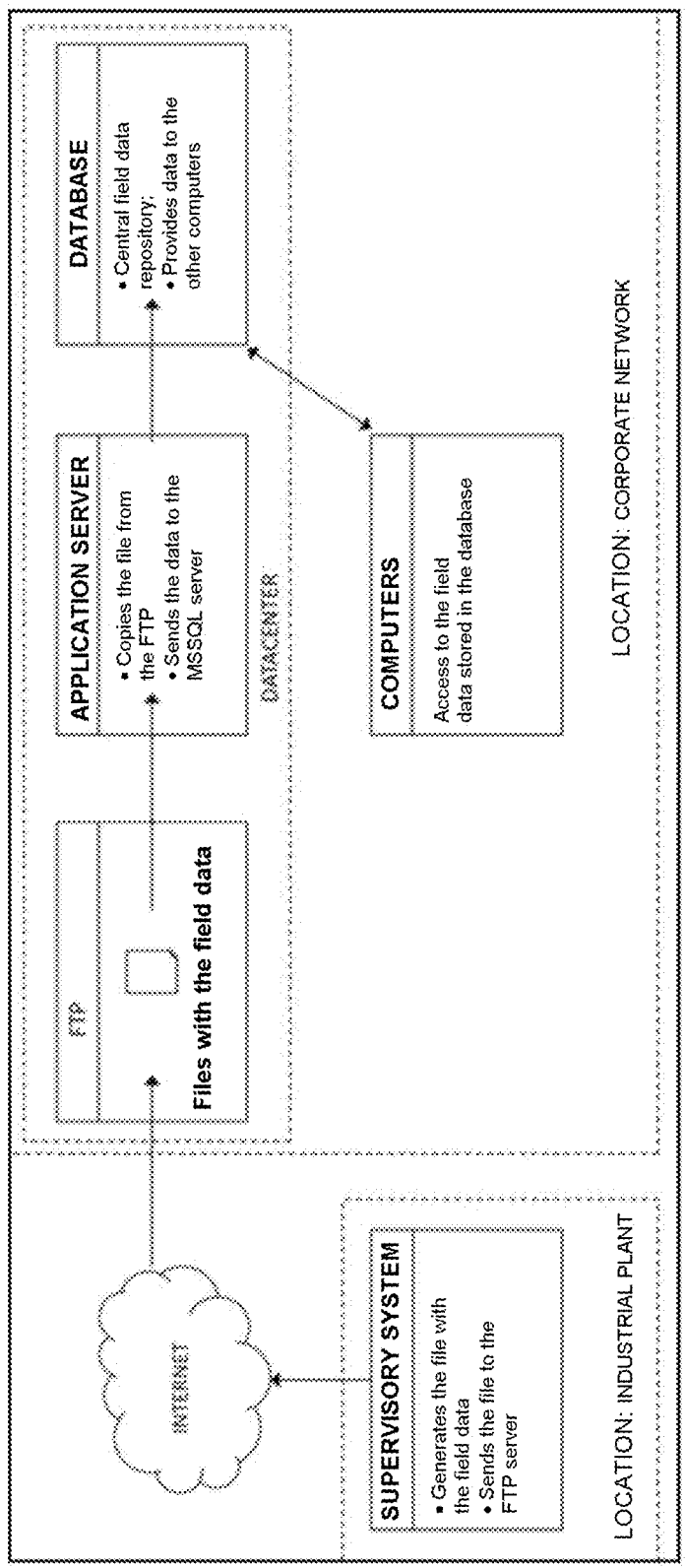
FIG. 3 illustrates a schematic flow diagram of the transmission of data from the mobile monitoring unit according to a specific configuration of the invention.

FIG. 3 shows a schematic flow diagram of the transmission of data from the mobile monitoring unit according to a specific configuration of the invention.

The automation of the unit permits the analyzers and other devices to operate as a remote data collection station. For the purposes of comprehension, the automation of the unit may be divided into two systems, that of control, principally constituted by the programmable logic controller, and the supervisory system.

The control system is installed in an automation panel, wherein is installed the PLC, the input and output modules (analogue and digital), the source of supply and the communication modules. The data from the analyzers of chlorine (amperometric and colorimetric), ammonia, biofilm formation, multiparameter probe and transmitters, together with the actuating signals of the valves and pumps, is received by the PLC and made available by the supervisory system connected to the PLC by means of Ethernet cable. In the left lateral door of the automation panel there is an emergency stop pushbutton, the actioning whereof results in the total shutdown of the unit.

In one possible embodiment the supervisory system is installed in a computer, functioning as a workstation within the interior of the container, wherein a proprietary application is installed permitting the creation of customized supervisory screens of the mobile monitoring unit, the monitoring whereof, in the field, renders possible that the selected and aforedescribed parameters, together with auxiliary functions such as solenoid valve actioning, alarms, etc, may be displayed.

The supervisory system receives all the data made available by the PLC and, by means of digital communication, the data from the deposition index analyzer and from the corrosimetric probes. The screens of the supervisory system display the functional status of the analyzers, of the instruments and of the pumps, in addition to permitting the activation and the control of the unit. Furthermore, the supervisory system possesses manual input for the insertion of the data required for the calculation of corrosion rate by the mass loss technique.

The data collected by the supervisory system is configured in an appropriate format and sent in a remote manner to an FTP server. In the application server, a routine of collection of data from the FTP server has been created, passing it on to the SQL server (database). This database stores in three different tables the readings of data realized by the analytical instruments installed in the mobile monitoring unit. This permits the control in real time of the parameters monitored in order to render possible a corrective or preventive action in the process taking advantage of the monitoring.

Another component to be emphasized is the internal temperature control of the monitoring unit. The potential action of technicians in the manipulation of samples and of liquids is rendered possible by means of a bench (sink).

By virtue of that set out hereinbefore it is clear that the mobile monitoring unit considers the following principal concepts: monitoring of corrosivity and of physicochemical and biological parameters, collection and transmission of remote data, unit for testing technologies, validation of alternative streams of water for cooling systems, and diagnostics and optimization of the chemical treatment employed.

Flowing therefrom, the invention incorporates unprecedented cooling water monitoring technologies in such manner as to provide the monitoring of the principal physicochemical parameters of control of the cooling water in industrial plants.

The remote collection of the data has been designed such as to permit the identification of changes in the control of the physicochemical parameters monitored as a response to events such as, for example, deficiencies in the treatment by chemical products or increase in the corrosion rate due to unexpected contamination. The collection of data from the analyzers is centralized in a man machine interface (MMI), the supervisory system whereof is responsible for the grouping of the data and the sending thereof, in an appropriate format, by cellular device to the FTP area.

The mobile monitoring unit described in the present memorandum has additionally been conceived as a pilot unit to test technologies associated with the chemical treatment of water and of effluents, in order to minimize the impacts upon the industrial plant, or to identify remote monitoring technologies the parameters whereof are relevant for monitoring the quality of water and of effluents. As a consequence, many characteristics described herein may be adapted in a manner such that the scope of protection of the invention is not restricted to the embodiment now described.

Furthermore, the mobile monitoring unit has been conceived with two centrifugal pumps 2 having the function of extracting water or effluent from the point of interest such as, for example, cooling water in the basins of cooling towers 1. Alternatively, extraction may be realized directly from an derivation available.

Following extraction, the water follows a circuit defined in a manner appropriate to the operational characteristics of each analyzer. A small volume may be discarded as a function of the operational characteristics of each analyzer. The stream of water, following passage through the analyzers, returns to the cooling tower 1 by means of pipework directed towards the basin of the cooling tower.

The unit possesses flexible hoses connected to the mobile monitoring unit and permitting the positioning of the unit at up to a distance of 50 m from the extraction point.

In addition, the supply is provided for of electric energy, directly or from an alternative generator. The possible preparation of test bodies or of reagent solutions may be executed upon the bench with sink.

Referring again to FIG. 1, it may be observed that in the configuration illustrated the mobile monitoring unit has been conceived in a container fitted with eight analytical instruments together with four test trees, rendering possible the monitoring of up to eleven parameters relating to the assessment of the physicochemical characteristics of cooling systems, having the objective, principally, of the reuse of water and of effluents in an autonomous manner and independent of the monitoring equipments employed by companies providing the services of water treatment.

By virtue of the aforedemonstrated characteristics, the mobile monitoring unit of the present invention may furthermore be utilized in diverse industrial plants making use of cooling water, having the objective of assessing the quality of that water.

The effluent cooling water from cooling systems may present contamination. This contamination may result in serious impacts upon the integrity of equipments of industrial plants, reducing the operational reliability and the working life of the equipments.

Consequently, the invention will be an essential tool in the selection of alternative sources of water for the replacement of cooling systems, rendering possible the planning of the reuse of water from different origins. It will also be possible to assess the impacts upon the integrity of the equipments immediately following the introduction of water or of effluent into the cooling system 1.

Specific adjustments in the chemical treatment of the cooling water will also be possible in order to ensure the efficacy thereof, simulating the specific operational conditions for the different characteristics of water and of effluents.

In addition, the mobile monitoring unit may also be used as a field research instrument by virtue of the fact that it incorporates concepts of mobility, flexibility, automation and data transmission.

The arrangement conceived will permit immediate adjustments in the dosage of chemical products based upon the monitoring of parameters, assessment and selection studies of chemical products in the field, permitting the utilization of replacement water from diverse origins, together with the reuse of effluents in cooling systems.

The invention is also revealed to be an efficacious tool in coping with scenarios of water scarcity, or zero discard, by virtue of the fact that the mobile monitoring unit renders possible the maximum utilization of aqueous streams, having the flexibility in the use of primary sources of water for application in industrial plants.

Therefore the continuous mobile monitoring unit of flowing cooling water is a pioneering project in water reuse.

Advantageously, the implementation of the mobile monitoring unit within industrial plants has been conceived in a manner such as not to impact upon the operating routine, through a compact structure, rendering viable rapid and integrated tests.

In addition, the invention renders possible a reduction in the demand for analyses in laboratories, whether owned or under contract, optimizing the monitoring and rendering possible better diagnostics of the quality of the water, by virtue of the fact that the data collected by the monitoring unit will be important in the selection and in the combination of water chemical treatment technologies in industrial plants requiring to reduce the corrosion in equipments and pipework, principally when the water arises from alternative sources, such as reused industrial water.

Rendering the system available will furthermore assist the processes of audit and control of the services provided in respect of water from cooling systems, by virtue of the fact that the invention includes sensors and equipments for the monitoring in real time of the quality of the water. The monitoring system is also an important research tool for validating and rendering viable cost reduction through the reuse of water, focusing upon regions wherein there exists water scarcity, resolving a technical need in this area.

Innumerable variations having a bearing upon the scope of protection of the present application are permissible. Consequently, the fact is emphasized that the present invention is not limited to the aforedescribed particular configurations/embodiments.

The invention claimed is:

1. A mobile monitoring unit of flowing cooling water, comprising:
a first pump configured to extract a flow of cooling water from a closed-loop cooling system to be analyzed;
at least one tank configured to analyze a plurality of parameters of the flow of cooling water by analytical techniques, generating results in relation to each one of the parameters analyzed;

a second pump configured to return the flow of cooling water to the closed-loop cooling system after the flow has been analyzed;

a system of operation and supervision constituted by at least one:

a supply panel;

an emergency electric supply;

a programmable logic controller;

a supervisory system;

a computer; and a modem.

2. The mobile monitoring unit of claim 1, wherein the parameters analyzed are selected from among: loss of mass from test bodies, rates of corrosion by corrosimetric probes, free residual chlorine, total residual chlorine, dissolved oxygen, pH, oxidation-reduction potential, conductivity, turbidity, biofilm formation, and index of deposition.

3. The mobile monitoring unit of claim 1, wherein the system of operation and supervision verifies whether the result of an analysis of each parameter of the cooling water is in conformity with a specification, and recommends a corrective action for each parameter of the cooling water falling outside the specification.

4. The mobile monitoring unit of claim 1, comprising a system of control interconnected with, and controlling, a plurality of valves, pumps and sensors adapted to manage the mobile monitoring unit.

5. The mobile monitoring unit of claim 1, wherein the means to tank comprises a plurality of sensors configured to detect the plurality of parameters.

6. The mobile monitoring unit of claim 1, wherein the mobile monitoring unit is constructed in an occupiable container structure.

7. The mobile monitoring unit of claim 1, further comprising tanks of chemical products adapted to carry out tests of performance of chemical products.

8. The mobile monitoring unit of claim 1, wherein the cooling water is collected downstream of the closed-loop cooling system and returns to the system at a point upstream or downstream of the closed-loop cooling system.

9. The mobile monitoring unit of claim 1, comprising at least one of: centrifugal pumps, hoses, dosing pumps of chemical products, air conditioning and bench with sink.

10. The mobile monitoring unit of claim 1, wherein the tank comprises a multiparameter probe, wherein the multiparameter probe is adapted to measure pH, turbidity, conductivity and oxidation-reduction potential.

11. The mobile monitoring unit of claim 1, wherein the system of operation and supervision is installed in an automation panel, wherein there is installed: a PLC, analogue and digital input and output modules, source of supply, and communication modules, wherein the PLC is adapted to receive data from amperometric or colorimetric chlorine analyzers, from ammonia analyzers, from biofilm formation analyzers, from a multiparameter probe, and from transmitters, together with an actuating signals of valves and pumps.

12. The mobile monitoring unit of claim 11, wherein the supervisory system is adapted to receive all data made available by the PLC and data from a deposition index analyzer and from a corrosimetric probes.

13. A method of continuous monitoring of flowing cooling water, the method comprising:

extracting a flow of cooling water from a closed-loop cooling system;

analyzing a plurality of parameters of the cooling water by diverse analytical techniques generating results related to each one of the parameters analyzed; and returning the flow of cooling water to the closed-loop cooling system.

14. The method of claim 13, wherein the parameters analyzed are selected from among: mass loss from test bodies, corrosion rates by corrosimetric probes, free residual chlorine, total residual chlorine, dissolved oxygen, pH, oxidation-reduction potential, conductivity, turbidity, biofilm formation and index of deposition.

15. The method of claim 13, comprising:

verifying whether the result of analyzing each parameter of the cooling water is in conformity with a specification and executing a corrective action for each parameter of the cooling water falling outside the specification, wherein each corrective action comprises an injection of a physicochemical agent into the flow of cooling water.

16. The method of claim 13, comprising discarding a portion of collected cooling water following an execution of at least one analysis of a parameter of the cooling water.

17. The method of claim 13, comprising measuring pH, turbidity, conductivity, and oxidation-reduction potential.

18. The method of claim 13 comprising control of an internal temperature of a mobile monitoring unit.

19. The mobile monitoring unit of claim 1, wherein the closed-loop cooling system comprises a cooling tower.

* * * * *